(12) United States Patent
Ishige et al.

(10) Patent No.: US 9,885,683 B2
(45) Date of Patent: Feb. 6, 2018

(54) ION-SELECTIVE ELECTRODE

(71) Applicant: Hitachi High-Technologies Corporation, Minato-ku, Tokyo (JP)

(72) Inventors: Yu Ishige, Tokyo (JP); Masao Kamahori, Tokyo (JP); Tetsuyoshi Ono, Tokyo (JP); Yusuke Goto, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 78 days.

(21) Appl. No.: 15/021,400

(22) PCT Filed: Jul. 28, 2014

(86) PCT No.: PCT/JP2014/069792
§ 371 (c)(1),
(2) Date: Mar. 11, 2016

(87) PCT Pub. No.: WO2015/045606
PCT Pub. Date: Apr. 2, 2015

(65) Prior Publication Data
US 2016/0223486 A1 Aug. 4, 2016

(30) Foreign Application Priority Data
Sep. 30, 2013 (JP) .............................. 2013-205646

(51) Int. Cl.
*G01N 27/333* (2006.01)
*G01N 27/30* (2006.01)

(52) U.S. Cl.
CPC ....... *G01N 27/3335* (2013.01); *G01N 27/308* (2013.01); *G01N 27/333* (2013.01)

(58) Field of Classification Search
CPC .................. G01N 27/333; G01N 27/3335
See application file for complete search history.

(56) References Cited

U.S. PATENT DOCUMENTS

| 4,454,007 A * | 6/1984 | Pace ................... G01N 27/3335 204/403.06 |
| 2003/0152486 A1 | 8/2003 | Yamashita et al. |

(Continued)

FOREIGN PATENT DOCUMENTS

| CN | 1737556 A | 2/2006 |
| CN | 102980931 A | 3/2013 |

(Continued)

OTHER PUBLICATIONS

Górski et al., "Influence of Inner Transducer Properties on EMF Response and Stability of Solid-Contact Anion Selective Membrane Electrodes Based on Metalloporphyrin Ionophores," J Solid State Electrochem. Jan. 1, 2009; 13(1): 157-164.*

(Continued)

*Primary Examiner* — Alexander S Noguerola
(74) *Attorney, Agent, or Firm* — Crowell & Moring LLP (57) ABSTRACT

To enhance the potential stability of a solid-electrode-type ion-selective electrode and reduce individual variations, the present invention is provided with an ion-sensitive membrane adapted to be in contact with a measurement solution, a mixture of graphite and liquid oil that is in contact with the ion-sensitive membrane, and a conductor that is in contact with the mixture of graphite and liquid oil.

9 Claims, 11 Drawing Sheets

(56) References Cited

U.S. PATENT DOCUMENTS

| | | |
|---|---|---|
| 2005/0000803 A1 | 1/2005 | Ritter et al. |
| 2008/0000290 A1 | 1/2008 | Nagels et al. |
| 2008/0293997 A1 | 11/2008 | Buhlmann et al. |

FOREIGN PATENT DOCUMENTS

| | | |
|---|---|---|
| DE | 100 18 750 C2 | 3/2003 |
| JP | 5-164725 A | 6/1993 |
| JP | 6-73045 A | 3/1994 |
| JP | 10-318973 A | 12/1998 |
| JP | 11-132991 A | 5/1999 |
| JP | 2000-146897 A | 5/2000 |
| JP | 2002-257781 A | 9/2002 |
| JP | 2003-207476 A | 7/2003 |
| JP | 2003-207481 A | 7/2003 |
| JP | 2004-340965 A | 12/2004 |
| JP | 2007-534949 A | 11/2007 |
| WO | WO 2005/103664 A2 | 11/2005 |

OTHER PUBLICATIONS

JPO computer-generated English language translation of JP 2000-146897 A. Downloaded Jul. 24, 2017.*

Chinese-language Office Action issued in counterpart Chinese Application No. 201480050487.2 dated Apr. 28, 2017 with English translation (15 pages).

International Search Report (PCT/ISA/210) issued in PCT Application No. PCT/JP2014/069792 dated Sep. 9, 2014 with English-language translation (four (4) pages).

Japanese-language Written Opinion (PCT/ISA/237) issued in PCT Application No. PCT/JP2014/069792 dated Sep. 9, 2014 (four (4) pages).

Y. Umezawa et al., "Potentiometric Selectivity Coefficients of Ion-Selective Electrodes Part I. Inorganic Cations," Pure Appl. Chem., vol. 72 (2000), No. 10, pp. 1851-2082.

Y. Umezawa et al., "Potentiometric Selectivity Coefficients of Ion-Selective Electrodes Part II. Inorganic Anions," Pure Appl. Chem., vol. 74 (2002), No. 6, pp. 923-994.

Extended European Search Report issued in counterpart European Application No. 14849328.1 dated May 24, 2017 (Eight (8) pages).

* cited by examiner

ION-SELECTIVE ELECTRODE

TECHNICAL FIELD

The present invention relates to an ion selective electrode used for measuring an electrolyte concentration in a solution.

BACKGROUND ART

An ion selective electrode (ISE) is dipped into a sample solution together with a reference electrode to measure a potential difference between the two electrodes and thus determine ions, which are measurement targets, in the sample. Due to the simplicity, the ISE is widely used in the field of analysis. In the field of medicine, the ISE is used for clinical laboratory tests and is used to measure an electrolyte not only with a dedicated device for measuring electrolytes but also with a biochemical automatic analysis device, an urgent sample testing device, or a point-of-care testing device.

The ISE uses an ion-sensitive membrane to selectively measure ions, which are the measurement targets, from a plurality of ions. An ion-sensitive membrane that is typically used is a membrane obtained by mixing a plasticizer and a ligand into a polymer-based substance such as polyvinyl chloride, and by further mixing a salt thereinto depending on cases. The ion-sensitive membrane generates a potential based on the Nernst equation in accordance with the concentration of ions that are the measurement targets. Thus, if one surface of the ion-sensitive membrane is allowed to contact an aqueous solution with a constant concentration and the other surface is allowed to simultaneously contact a sample solution, it is possible to obtain electromotive force in accordance with the concentration of ions that are the measurement targets in the sample solution. The concentration of ions, which are the measurement targets, is calculated from the obtained electromotive force. Such an electrode with a structure in which a side of a sensitive membrane that is on the opposite side of a sample solution is filled with an aqueous solution or gel is called an internal-liquid-type ISE.

In contrast to the internal-liquid-type ISE, an electrode with a structure in which a surface of a sensitive membrane on the opposite side of a sample solution is allowed to be in direct contact with a conductive electrode is called a coated wire-ion selective electrode (CW-ISE) or a solid contact-ion selective electrode (SC-ISE). Herein, such electrodes are referred to as solid electrodes. Since solid electrodes do not require an internal solution, such electrodes can be easily reduced in size and have been applied to point-of-care testing devices. For an electrode (base electrode) that is allowed to be in contact with a sensitive membrane, platinum, silver chloride covered with a conductive polymer, gold modified with a monomolecular film, porous carbon, carbon black, or a mixture of a polymer and graphite has been used.

CITATION LIST

Patent Literature

Patent Literature 1: JP 2007-534949A (WO 2005/103664)

SUMMARY OF INVENTION

Technical Problem

The inventors have conducted research and development to devise a solid-electrode-type ISE with high potential stability and small individual variations. As a consequence, it has been found to be impossible to obtain both sufficient potential stability and small individual variations with the conventional methods.

As a result of examining a factor, it has been found that ions that control a potential between a base electrode and a sensitive membrane and ions that control a potential between the sensitive membrane and a sample solution are different or unknown. For example, when gold covered with a monomolecular film is used for the base electrode, a potential between the sensitive membrane and the base electrode is controlled by the transfer of electrons that occurs in redox reactions, while a potential between the sensitive membrane and the sample solution is controlled by the ions that are the measurement targets, for example, potassium ions.

Solution to Problem

The ISE in accordance with the present invention includes a mixture of graphite and liquid oil as abuse electrode.

That is, the ISE in accordance with the present invention is an electrode for selectively detecting an ion as a measurement target in a measurement solution, and includes an ion-sensitive membrane adapted to be in contact with the measurement solution, a mixture of graphite and liquid oil, the mixture being in contact with the ion-sensitive membrane, and a conductor in contact with the mixture of graphite and liquid oil.

As an example, the ion-sensitive membrane includes a plasticizer and the liquid oil includes the same plasticizer.

As an example, a relative difference between a weight ratio of the plasticizer included in the ion-sensitive membrane and a weight ratio of the plasticizer included in the mixture of graphite and liquid oil is 30% or less.

As an example, the ion-sensitive membrane includes a hydrophobic anion, and the mixture of graphite and liquid oil includes the same hydrophobic anion.

As an example, the ion-sensitive membrane includes a substance that selectively binds to the ion as the measurement target, and the mixture of graphite and liquid oil includes the same substance.

As an example, the liquid oil is a fluorine-based polymer or a fluorine-based oil.

As an example, the graphite is synthetic graphite.

Advantageous Effects of Invention

According to the present invention, as a mixture of graphite and liquid oil is used for a base electrode, the base electrode responds to monovalent cations, such as lithium, potassium, and sodium, which are the measurement target ions. Thus, if a sensitive membrane that is sensitive to monovalent cations is used, potentials on the opposite sides of the sensitive membrane are controlled by the same ions. Thus, sufficient potential stability and low individual variations can be obtained.

With a mixture of graphite and liquid oil, it is possible to produce uniform mixtures at a time and thus to produce a plurality of base electrodes with identical components. Therefore, individual variations can be reduced.

When a plasticizer included in the ion-sensitive membrane is used as the liquid oil, it is possible to suppress a potential fluctuation due to the diffusion of the plasticizer from the ion-sensitive membrane to the base electrode, thereby improving the potential stability. Further, when a salt or a ligand, which is a compound included in the ion-sensitive membrane, is added to the base electrode, it becomes possible to maintain preferable individual variations even after the passage of time.

When a mixture of graphite and a fluorine-based polymer is used for the base electrode, it is possible to prevent the diffusion of components, such as the plasticizer, included in the ion-sensitive membrane to the base electrode while at the same time maintaining the response to monovalent cations.

When synthetic graphite is used as the graphite, the base electrode will include no carbon, which has various functional groups on its surface, of the natural graphite. As a consequence, side reactions due to such carbon can be suppressed and the potential stability can thus be obtained.

Problems, configurations, and advantageous effects other than the foregoing will become apparent from the following description of embodiments.

DESCRIPTION OF EMBODIMENTS

Embodiments of the present invention will be hereinafter described with reference to the attached drawings.

Figure 1A:
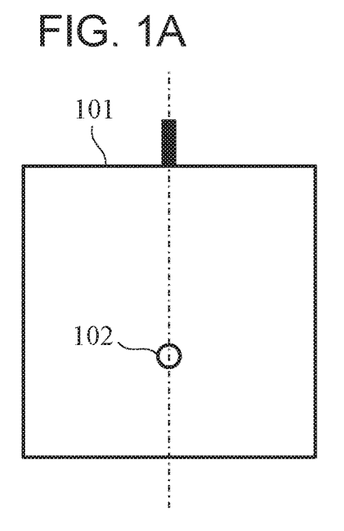
FIGS. 1A-1C show schematic diagrams illustrating an example of a solid-electrode-type ISE.
Figure 1B:
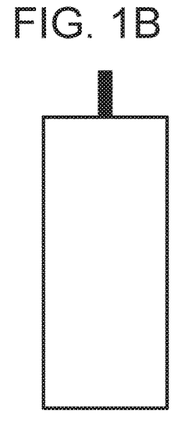
Figure 1C:
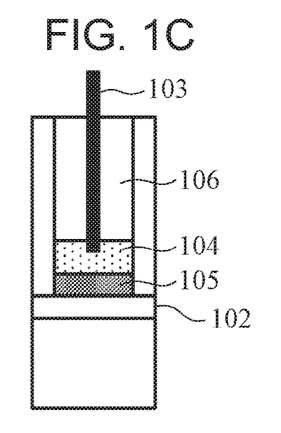

FIG. 1 shows schematic diagrams illustrating an example of a solid-electrode-type ISE. A flow channel 102 passes through a cartridge 101 of the ISE. FIG. 1(a) illustrates a plane perpendicular to the flow channel, and FIG. 1(b) illustrates a plane parallel with the flow channel. FIG. 1(c) illustrates a cross-section along a chain line in FIG. 1(a), in which a sensitive membrane 105 is in contact with the flow channel, the opposite side of the flow channel is filled with a mixture 104 of graphite and liquid oil, and a platinum wire 103 is in contact with the mixture 104. The platinum wire 103 also functions as a terminal. It is possible to use, as the sensitive membrane 105, an ion-selective membrane made of lithium, sodium, or potassium described in Pure Appl. Chem., Vol. 72, No. 10, pp. 1851-2082, 2000.

An example of a method of producing the ISE in FIG. 1 will be described. The sensitive membrane 105 is attached to the cartridge 101 made of resin such as polyvinyl chloride, polystyrene, or polypropylene. A solvent such as tetrahydrofuran may be used for the attachment. Alternatively, mechanical pressure may be applied for the attachment. Next, the mixture 104 of graphite and liquid oil is arranged on the sensitive membrane 105. For the mixture 104 of graphite and liquid oil, graphite and liquid oil are mixed at a weight ratio of 1:2, and are further stirred sufficiently with a mortar. A cover 106 is put, and the platinum wire 103 is inserted from a hole in the cover 106 so as to contact the mixture 104 of graphite and liquid oil, thereby realizing electric connection therebetween.

The liquid oil is preferably in a liquid state at 0° C. to 50° C. that are the assumed usage environment. This is because if the liquid oil is in a liquid state, the response to monovalent cations, which will be described later, is expected, the adhesion to the sensitive membrane can be maintained, and the movement, if any, of ions in the liquid can be increased in speed, thereby improving the responsiveness. If the liquid oil is a liquid under the usage conditions, the liquid oil need not be liquid over the entire temperature range. For the liquid oil, it is possible to use a substance that is not miscible with water, for example, alkane such as paraffin, plasticizer such as DOA, DOP, DOS, or oNPOE described in Pure Appl. Chem., Vol. 72, No, 10, pp. 1851-2082, 2000, a fluorine-based polymer, or fluorine-based oil.

Figure 2A:
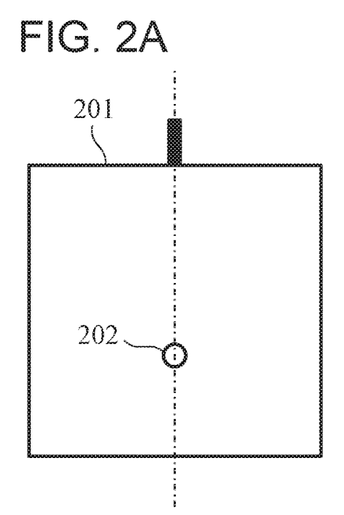
FIGS. 2A-2C show schematic diagrams illustrating an example of an internal-liquid-type ISE.
Figure 2B:
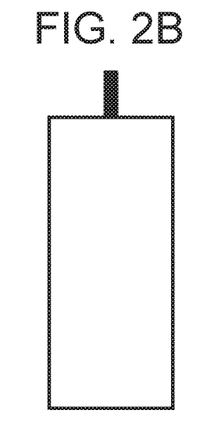
Figure 2C:
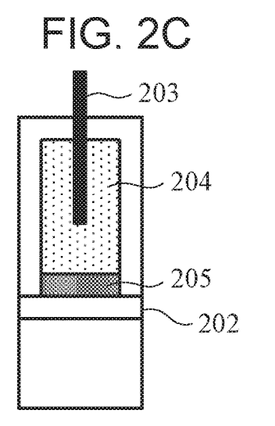

FIG. 2 shows schematic diagrams illustrating an example of an internal-liquid-type ISE used for comparison purposes. A flow channel 202 passes through a cartridge 201 of the ISE. FIG. 2(a) illustrates a plane perpendicular to the flow channel, and FIG. 2(b) illustrates a plane parallel with the flow channel. FIG. 2(c) illustrates a cross-section along a chain line in FIG. 2(a). A sensitive membrane 205 is in contact with the flow channel, and the opposite side of the flow channel is filled with an internal solution 204. A silver-silver chloride electrode 203 is in contact with the internal solution 204. The silver-silver chloride electrode 203 also functions as a terminal. In case of a cation selective electrode made of sodium, potassium, calcium, magnesium, or the like, it is possible to use a membrane described in Pure Appl. Chem., Vol. 72, No. 10, pp. 1851-2082, 2000, for example, as the sensitive membrane 205. In case of an anion selective electrode made of chlorine, carbonic acid, thiocyanogen, nitric acid, hydroxyl, phosphate, sulfuric acid, iodine, or the like, it is possible to use a membrane described in Pure Appl. Chem., Vol, 74, No. 6, pp. 923-994, 2002, silver halide such as silver chloride or silver bromide, or an ion-exchange membrane (JP H10-318973A, JP H11-132991A, JP2003-207476A). In case of a reference electrode, it is possible to use porous glass, ceramics, or the like.

Figure 3:
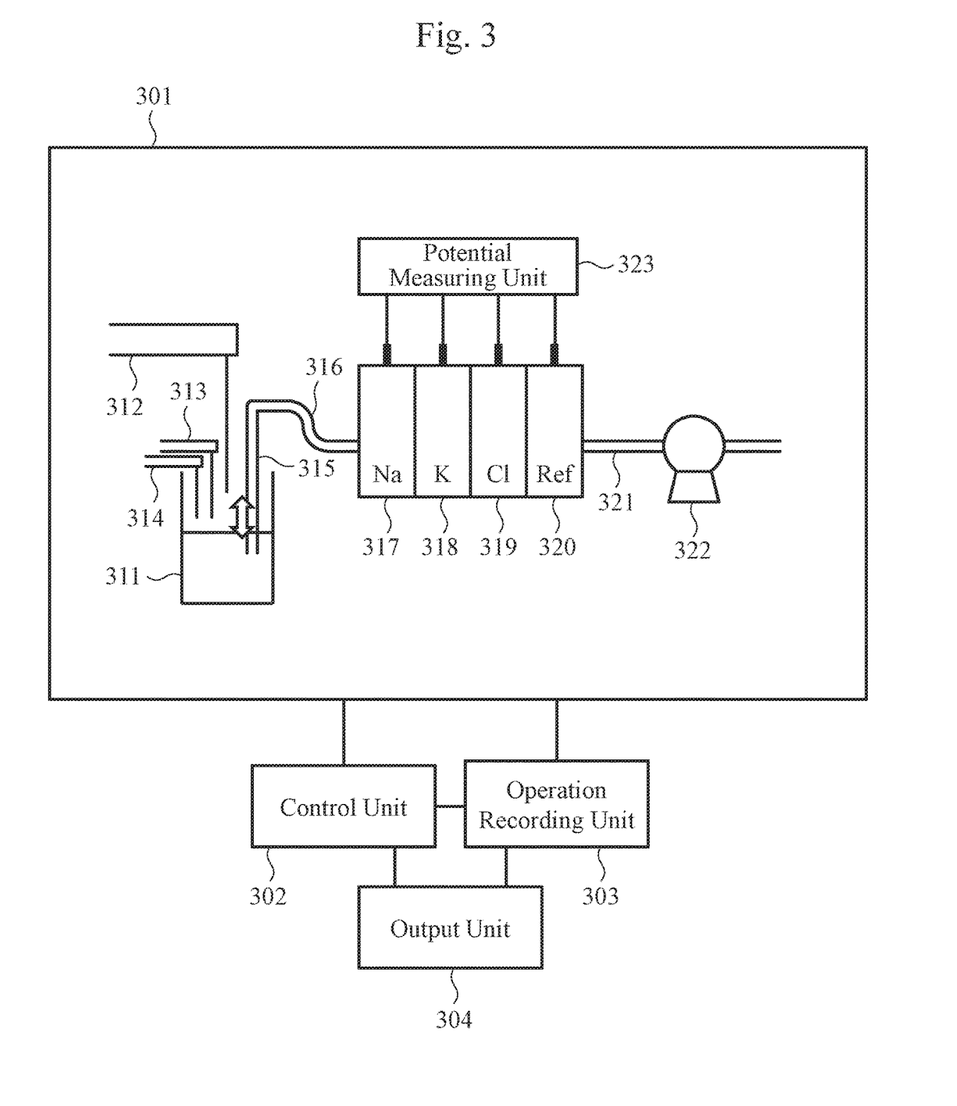
FIG. 3 is a schematic diagram illustrating an example of an electrolyte measuring device.

FIG. 3 is a schematic diagram illustrating an example of an electrolyte measuring device that uses the ISE in FIG. 1 or FIG. 2. A control unit 302, an operation recording unit 303, and an output unit 304 are connected to a measuring unit 301. The measuring unit 301 includes a dilution tank 311, a sample dispensing nozzle 312, a diluent dispensing nozzle 313, an internal-standard-solution dispensing nozzle 314, a suction nozzle 315, a pipe 316, a sodium ISE 317, a potassium ISE 318, a chlorine ISE 319, a reference electrode 320, a pipe 321, a pump 322, and a potential measuring unit 323. The sample dispensing nozzle 312, the diluent dispensing nozzle 313, and the internal-standard-solution dispensing nozzle 314 dispense and discharge, to the dilution tank 311, a sample such as blood or urine, a diluent, and an internal-standard-solution, respectively. The diluent does not contain the measurement target ions or has a known, low concentration, and can be used for diluting the sample. The internal-standard-solution is a sample with a known ion concentration, and can be used for calibrating potentials. The sample solution suction nozzle 315 can be moved up and down, and a solution in the dilution tank 311 is sucked with the drive force of the pump 322. The sucked solution is introduced into flow channels of the electrodes 317 to 320 via the pipe 316, and is further discharged via the pipe 321. The terminal of each electrode is connected to the potential measuring unit 323.

Figure 4:
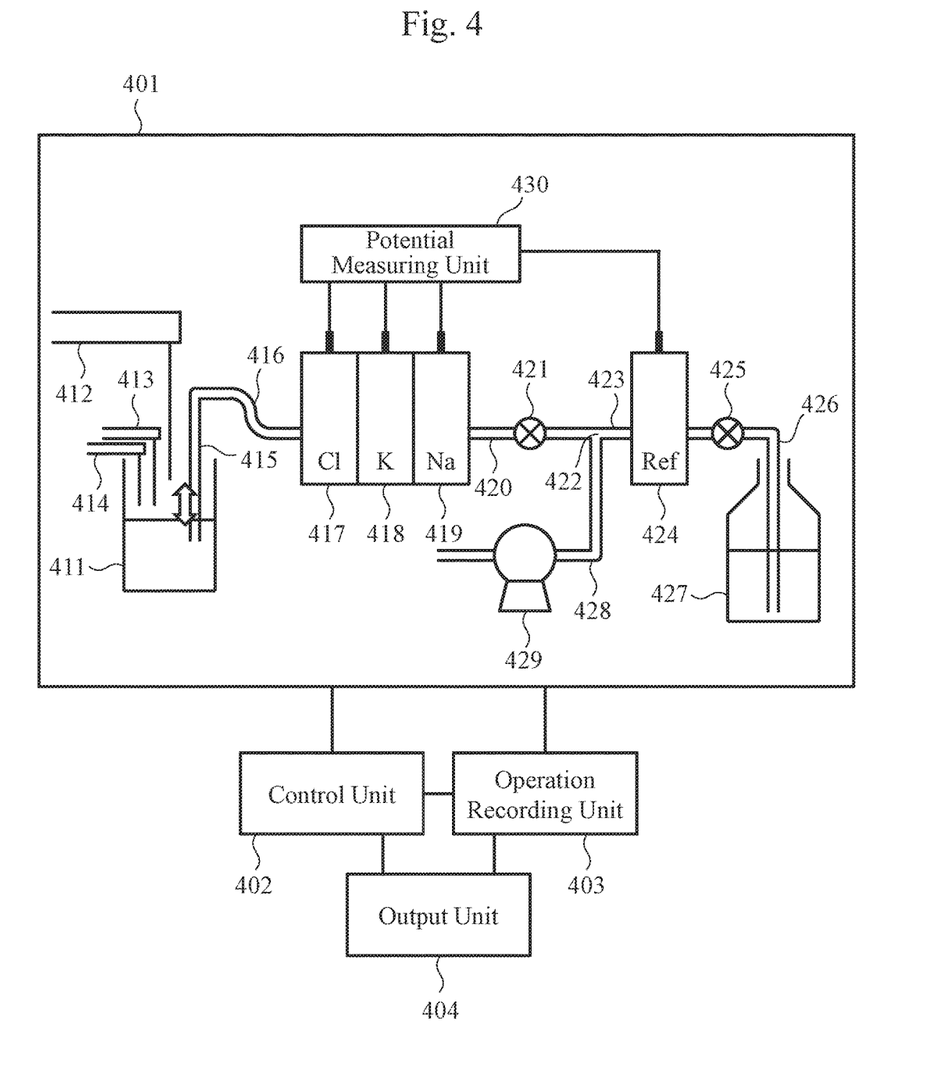
FIG. 4 is a schematic diagram illustrating another example of the electrolyte measuring device.

FIG. 4 is a schematic diagram illustrating another example of the electrolyte measuring device that uses the ISE in FIG. 1 or FIG. 2. A control unit 402, an operation recording unit 403, and an output unit 404 are connected to a measuring unit 401. The measuring unit 401 includes a dilution tank 411, a sample dispensing nozzle 412, a diluent dispensing nozzle 413, an internal-standard-solution dispensing nozzle 414, a suction nozzle 415, a pipe 416, a chlorine ISE 417, a potassium ISE 418, a sodium ISE 419, a pipe 420, a valve 421, a junction 422, a pipe 423, a reference electrode 424, a valve 425, a pipe 426, a reference solution 427, a pipe 428, a pump 429, and a potential measuring unit 430. The sample dispensing nozzle 412, the diluent dispensing nozzle 413, and the internal-standard-solution dispensing nozzle 414 dispense and discharge, to the dilution tank 411, a sample such as blood or urine, a diluent, and an internal-standard-solution, respectively. The sample solution suction nozzle 415 can be moved up and down, and sucks a solution in the dilution tank 411 with the drive force of the pump 429.

When the valve 421 is open and the valve 425 is closed, the sucked solution is introduced into flow channels of the electrodes 417 to 419 via the pipe 416, and is further discharged via the pipe 420, the junction 422, and the pipe 428. Meanwhile, when the pump 429 is driven with the valve 421 closed and the valve 425 open, the reference solution 427 is sucked via the pipe 426 and is introduced into a flow channel of the reference electrode 424. Further, the reference solution 427 is discharged via the pipe 423, the junction 422, and the pipe 428. Terminals of the electrode 417 to 419 and 424 are connected to the potential measuring unit 430. For the potential measuring unit 430, a potential measuring unit similar to that in FIG. 3 can be used. In addition to using a reference electrode, which is formed using porous glass or ceramics described with reference to FIG. 2, for the reference electrode 424, it is also possible to use an ISE for the reference electrode 424, and set the electrolyte concentration in the corresponding reference solution 427 constant.

Figure 5A:
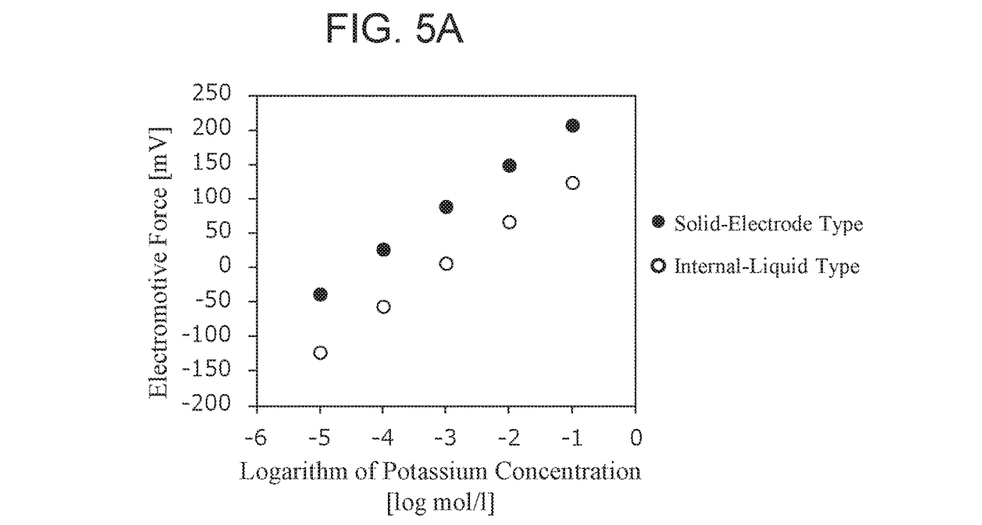
FIGS. 5A and 5B illustrate examples of measurement results of the electrolyte concentration.
Figure 5B:
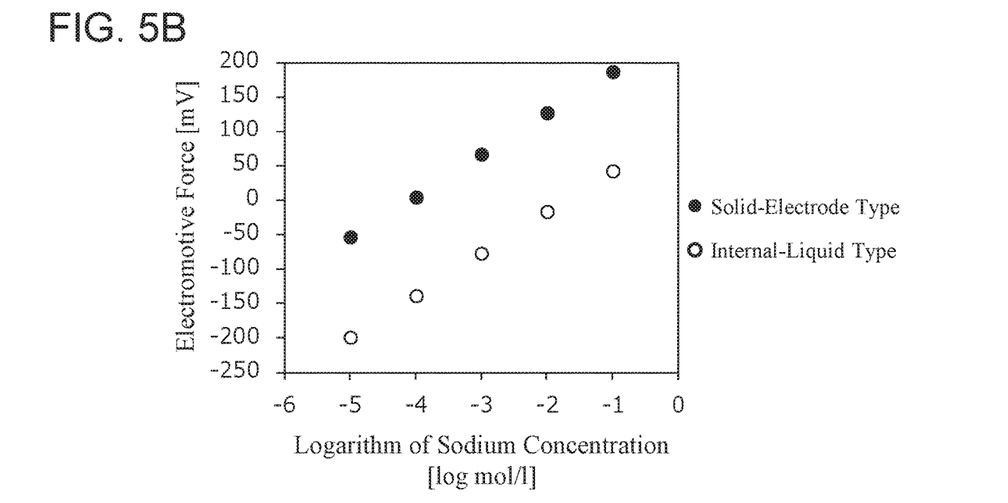

FIG. 5 illustrates examples of results of measuring the electrolyte concentration using the solid-electrode-type ISE in accordance with the present invention and the conventional internal-liquid-type ISE. A potassium ion-selective membrane contains 30% w/w polyvinyl chloride (PVC) as a base substance, 66% w/w oNPOE as a plasticizer, a Bis (benzo-15-crown-5) as a ligand (substance that selectively binds to an ion as a measurement target), and tetraphenyl borate potassium (KTpClPB), which is a salt of a hydrophobic anion excluder, as an anion excluder. A sodium ion-selective membrane contains 30% w/w polyvinyl chloride (PVC) as a base substance, 66% w/w oNPOE as a plasticizer, Bis(12-crown-4) as a ligand (substance that selectively binds to an ion as a measurement target), and a Tetrakis[3,5-bis(trifluorinemethyl)phenyl]borate, sodium salt (NaTFPB), which is a salt of a hydrophobic anion as an anion excluder. A mixture containing natural graphite (CAS. No. 7782-42-5) and paraffin oil (CAS. No. 8042-47-5) at a weight ratio of 1:2 was used for the base electrode.

FIG. 5(a) illustrates a result of measuring a potassium chloride aqueous solution by using the potassium ISE for the sensitive membrane. FIG. 5(b) illustrates a result of measuring a sodium chloride aqueous solution by using the sodium ISE for the sensitive membrane. Both the results are found to exhibit 61.6 mV/decade that is identical to the theoretical value. As mentioned above, the solid-electrode-type ISE in accordance with the present invention can obtain the same potential response as that of an internal-liquid-type ISE.

Similarly, five solid-electrode-type potassium ISEs were produced, and potentials when 10 mmol/l potassium chloride aqueous solutions were measured were compared with each other. Accordingly, it is found that the standard deviation of the potentials is as low as 3.6 mV that is a practically allowable level, and thus that the solid-electrode-type ISE in accordance with the present invention can have suppressed individual variations in potentials. As a reason that individual variations can be suppressed, it is considered that a mixture of graphite and liquid oil, which is the base electrode, has responsiveness to monovalent cations that are the measurement target ions.

Figure 6A:
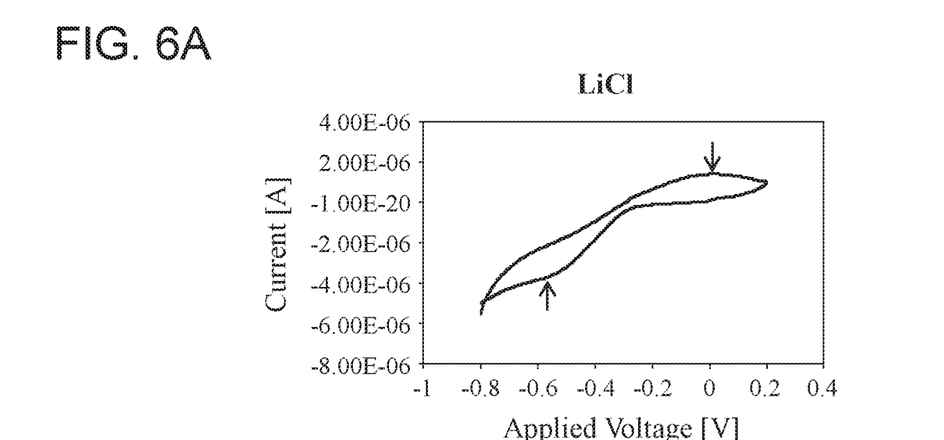
FIGS. 6A-6C illustrate measurement results that show the responsiveness to monovalent cations of a mixture of graphite and liquid oil.
Figure 6B:
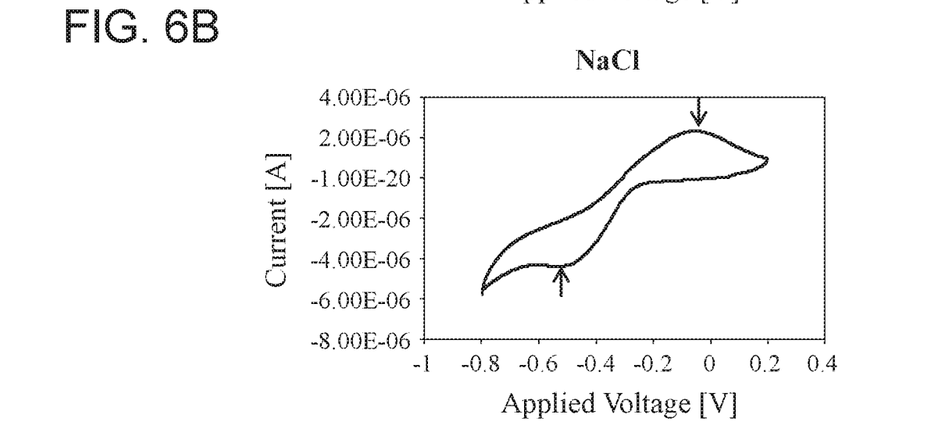
Figure 6C:
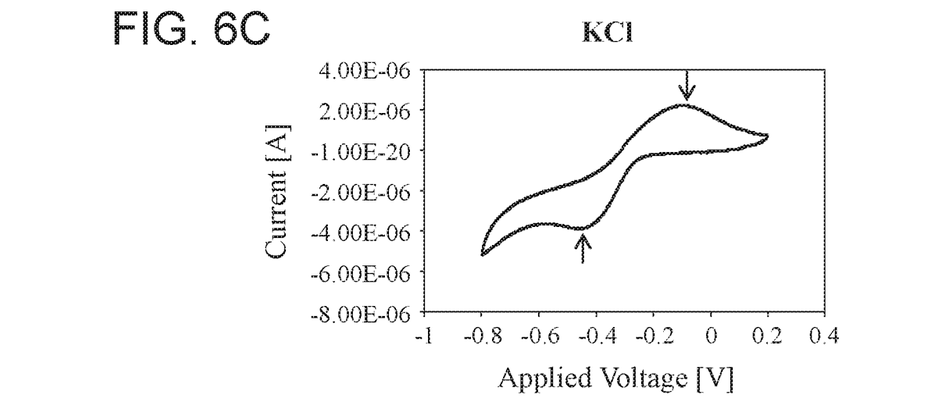

FIG. 6 illustrates measurement results that show that a mixture of graphite and liquid oil has responsiveness to monovalent cations. Using a potentiostat, and using a mixture of graphite and liquid oil (without a sensitive membrane) as a working electrode; a silver-silver chloride reference electrode, which uses saturated potassium chloride as an internal solution, as a reference electrode; and a platinum electrode, as a counter electrode, measurement was conducted in a 100 mmol/l lithium chloride aqueous solution (FIG. 6(a)), a 100 mmol/l sodium chloride aqueous solution (FIG. 6(b)), and a 100 mmol/l potassium chloride aqueous solution (FIG. 6(c)). As a measuring condition, the sweep rate was set to 100 mV/s. As a consequence, current peaks were observed at around −0.5 V and 0 V under any one of the conditions in FIGS. 6(a) to 6(c) Such peaks are considered to be due to the uptake and release of cations into/from the mixture of graphite and liquid oil.

Figure 7A:
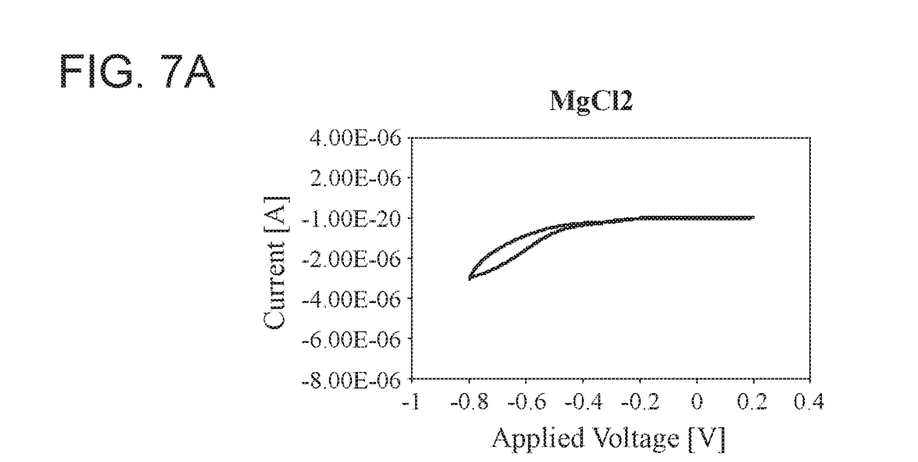
FIGS. 7A-7C illustrate measurement results that show the responsiveness to divalent cations of the mixture of graphite and liquid oil.
Figure 7B:
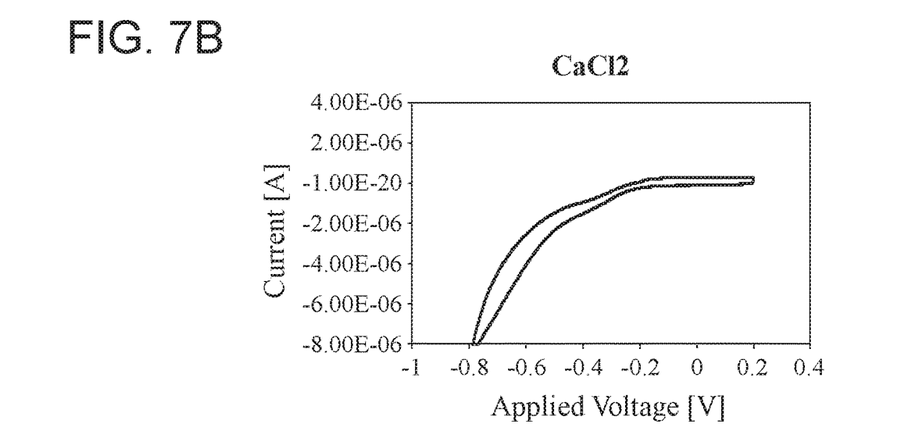
Figure 7C:
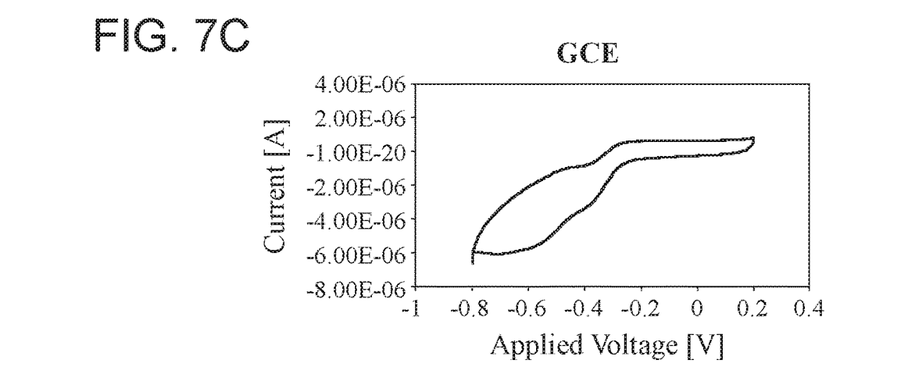

Meanwhile, when measurement was conducted with a 100 mmol/l magnesium chloride aqueous solution (FIG. 7(a)) and a 100 mmol/l calcium chloride aqueous solution, no current peaks corresponding to the uptake and release of ions were observed (FIG. 7(b)). When measurement was conducted with a 100 mmol/l potassium chloride aqueous solution using a glassy carbon electrode (FIG. 7(c)), no current peaks corresponding to the uptake and release of ions were observed, either.

That is, a mixture of graphite and liquid oil has responsiveness to monovalent cations, and has low responsiveness to divalent cations.

Figure 8:
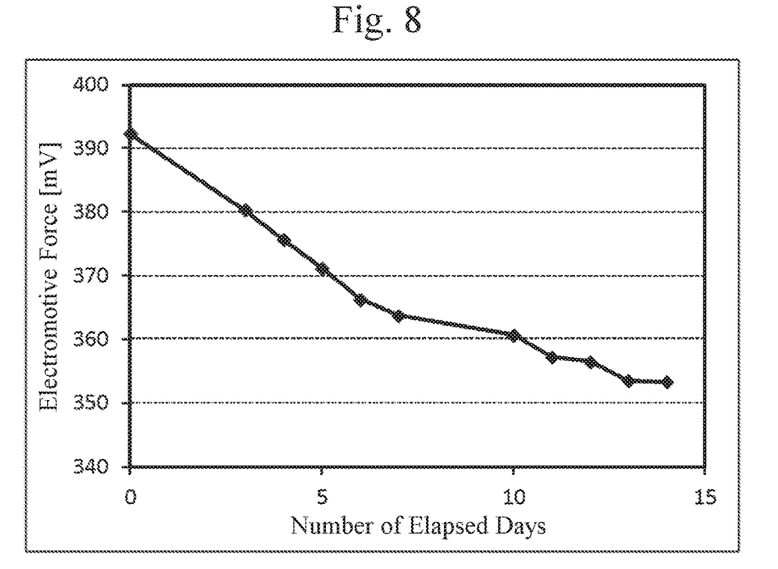
FIG. 8 illustrates changes per day of the potential of a solid electrode.

FIG. 8 illustrates an example of changes per day of the electromotive force to a similarly produced solid-electrode-type potassium ISE, which uses a mixture of natural graphite and paraffin oil as a base electrode, against a 100 mmol/l potassium chloride aqueous solution. It is found that the electromotive force gradually decreases with each day. This is estimated to be due to impurities in the natural graphite and the diffusion of paraffin oil in the base electrode into the ion-sensitive membrane.

Figure 9:
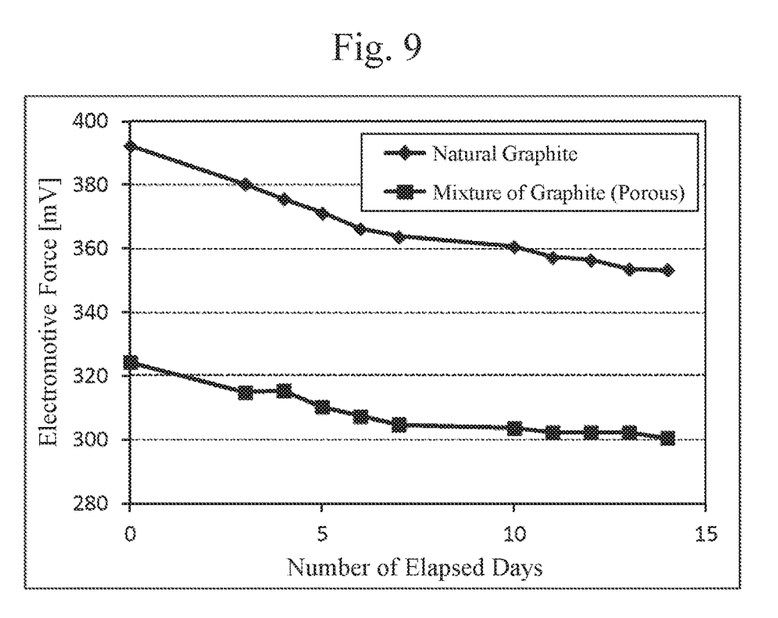
FIG. 9 illustrates changes per day of the potential of solid electrodes.

As a countermeasure against impurities in the graphite, synthetic graphite (CAS. No. 1333-86-4) was used in place of the natural graphite. FIG. 9 illustrates the results. It is found that the use of the synthetic graphite allows a reduction of a potential. This is considered to be due to the influence of carbon, which has various functional groups on its surface, of the natural graphite.

Figure 10:
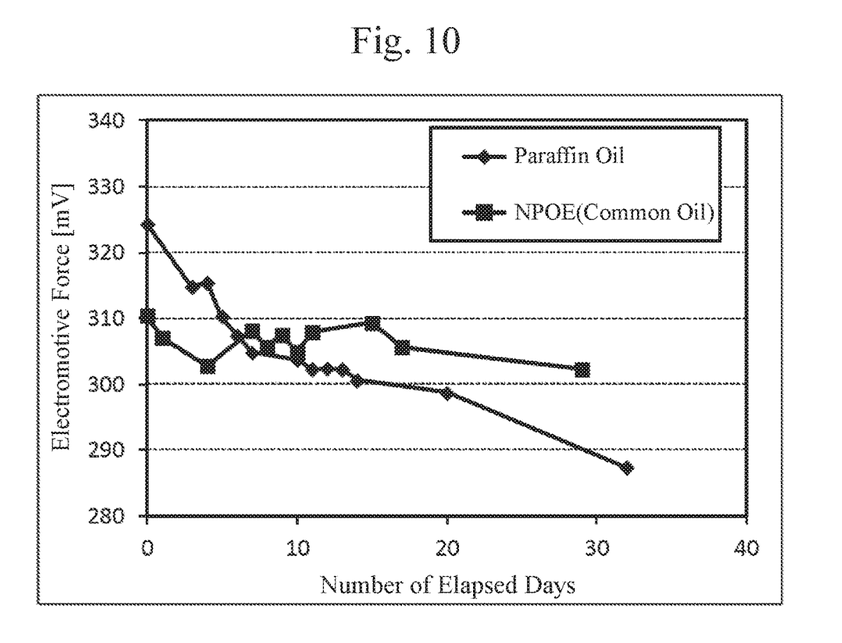
FIG. 10 illustrates changes per day of the potentials of solid electrodes.

As a countermeasure against the diffusion of paraffin oil into the ion-sensitive membrane, a plasticizer that is the main component of the ion-sensitive membrane (in this case, oNPOE) was used in place of the paraffin oil. FIG. 10 illustrates the results. It is found that the reduction in the potentials is suppressed to ¼. This is estimated to be due to the reason that the diffusion of oil was suppressed as the same oil was used for the base electrode and the ion-sensitive membrane. If the plasticizer used for the ion-sensitive membrane is a different plasticizer such as DOA, DOP, or DOS as described in Pure Appl. Chem., Vol. 72, No. 10, pp. 1851-2082, 2000, the same effect is obtained by using the same plasticizer as that of the ion-sensitive membrane for the base electrode.

Figure 11:
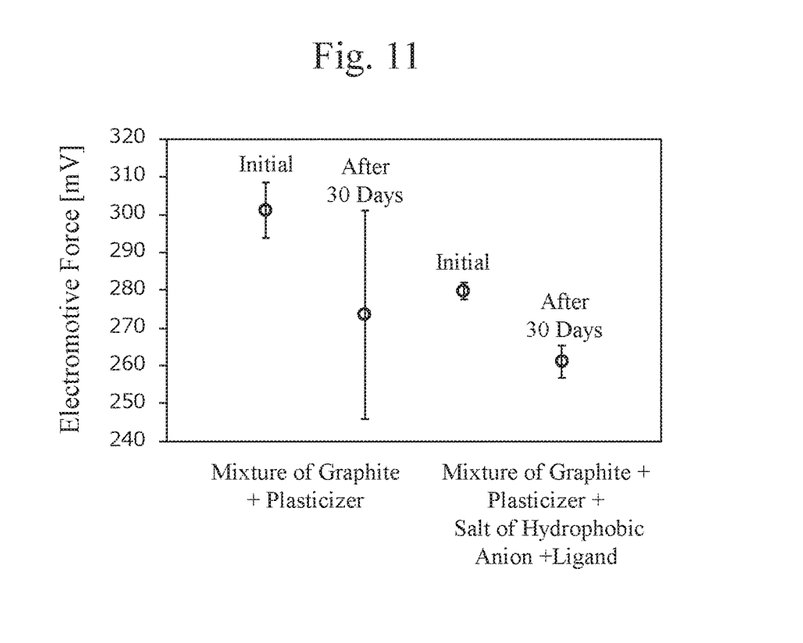
FIG. 11 illustrates individual variations of the potentials of solid electrodes.

FIG. 11 illustrates examples of changes per day of the electromotive force of a solid-electrode-type ISE, which is formed using a mixture of synthetic graphite and a plasticizer (in this case, oNPOE) or a mixture of synthetic graphite, a plasticizer, and a salt of a hydrophobic anion (in this case. NaTFPB), and a ligand (in this case, Bis(12-crown-4)), as a base electrode, and uses a similar sodium selective membrane to that described above for the sensitive membrane, against a 100 mmol/l sodium chloride aqueous solution. If a mixture of synthetic graphite and a plasticizer was used for the base electrode, the standard-deviation, which had been as low as 7.3 mV just after the preparation of the ISE, increased to 28 mV after 30 days have passed. In contrast, if a mixture of synthetic graphite, a plasticizer, a salt, and a ligand was used for the base electrode, the standard deviation, which had been as low as 2.3 mV just after the preparation of the ISE, remained as low as 3.9 mV even after 30 days has passed. This is estimated to be due to the reason that as the base electrode contains the same substances as the salt and the ligand contained in the sensitive membrane at the same concentrations, diffusion of the salt and the ligand was suppressed. As the salt contained in each of the base electrode and the sensitive membrane, it is possible to use a salt of a hydrophobic anion, such as KTFPB, KTmClPB, KTPB, KTpClPB, NaTFPB, or NaTp-ClPB described in Pure Appl, Chem., Vol. 72, No. 10, pp. 1851-2082, 2000. As the ligand (substance that selectively binds to a measurement target) contained in each of the base electrode and the sensitive membrane, it is possible to use Valinomycin described in Pure Appl. Chem., Vol. 72, No. 10, pp. 1851-2082, 2000, a crown ether compound, or their equivalents.

When a plasticizer is used as the liquid oil, the concentration in terms of weight % of the plasticizer in the sensitive membrane is 33% or more in order to prevent a significant reduction in the resistance, and is 70% or less in order to prevent a significant reduction in the mechanical strength, and is, depending on cases, in the range of 40% to 70%, 50% to 70%, or 60% to 70%, or preferably be 66% in order to reduce the resistance. In that case, the concentration in terms of weight % of the plasticizer in the base electrode is in the range of 33% to 80%, 40% to 80%, 50% to 80%, or 60% to 80%, or preferably, 66% in keeping with the concentration of the plasticizer in the sensitive membrane. Preferably, the ratio, in terms of weight %, between the concentration of the plasticizer in the sensitive membrane and the concentration of the plasticizer in the base electrode is within ±30%, ±20%, ±10%, ±5%, ±3%, or ±1%, or preferably, within ±1%.

Figure 12:
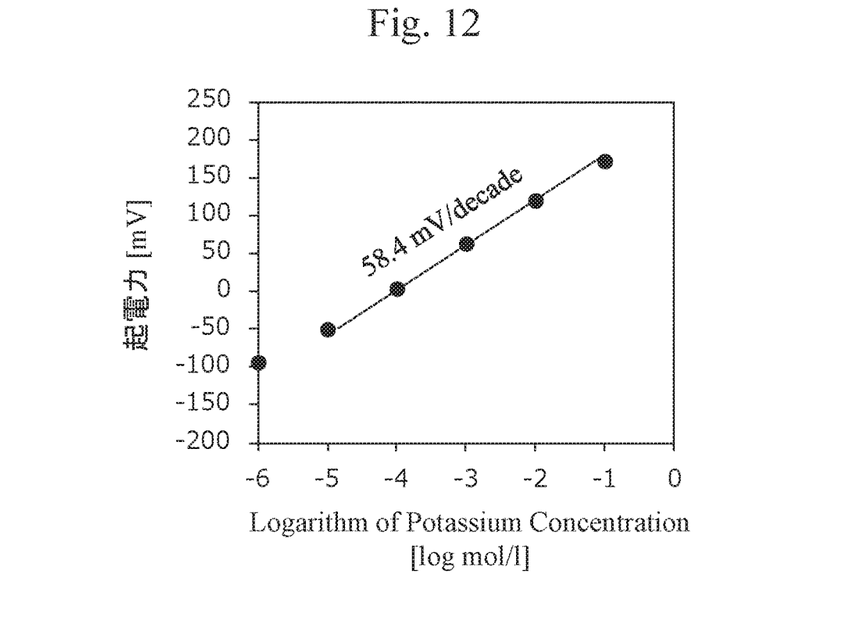
FIG. 12 illustrates an example of a measurement result of the electrolyte concentration
Figure 13:
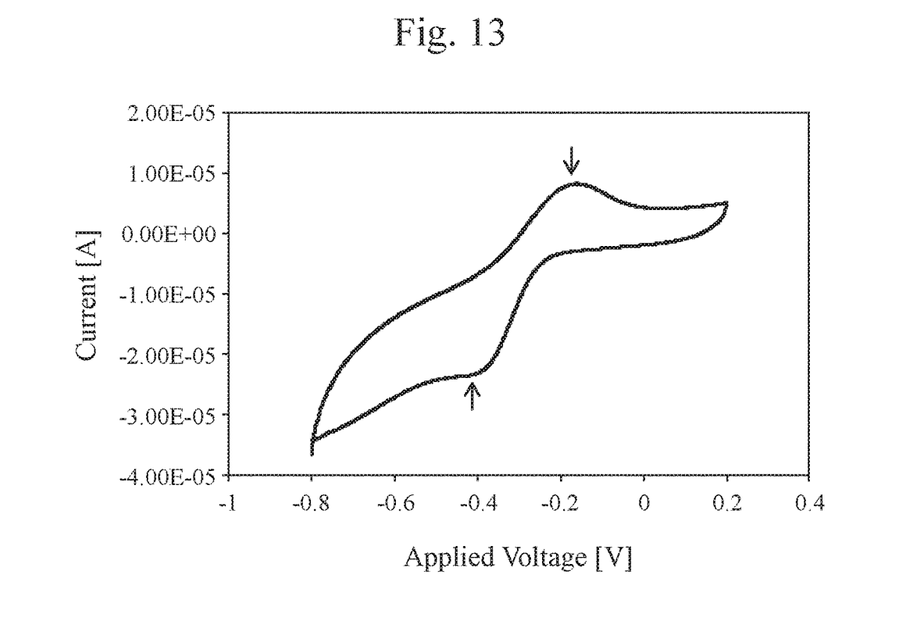
FIG. 13 illustrates a measurement result that shows the responsiveness to monovalent cations of a mixture of graphite and liquid oil.

FIG. 12 illustrates an example of measuring the electrolyte concentration using the solid-electrode-type ISE in accordance with the present invention, A mixture of natural graphite (CAS. No. 7782-42-5) and a fluorine-based polymer (FOMBLIN®) was used for the base electrode, and the aforementioned potassium selective membrane was used for the sensitive membrane. When a potassium chloride aqueous solution was measured under a condition of 25° C., a potential response of 58.4 mV/decade, which is identical to the theoretical value, was obtained. By using a fluorine-based polymer for the base electrode, it is possible to prevent a component, which can cause a potential fluctuation, in the sensitive membrane from being diffused into the base electrode. Meanwhile, FIG. 13 can confirm that the response to monovalent cations, which has been observed in FIG. 6, is maintained. FIG. 13 illustrates a result of conducting measurement in a 100 mmol/l potassium chloride aqueous solution using a potentiostat, and using a mixture of graphite and a fluorine-based polymer for a working electrode; a silver-silver chloride reference electrode, which uses saturated potassium chloride as an internal solution, for a reference electrode; and a platinum electrode for a counter electrode. Current peaks were observed at around −0.4 V and −0.2 V.

When a fluorine-based polymer is used as the liquid oil, the concentration in terms of weight % of a fluorine-based polymer in the base electrode is 33% to 80%, 40% to 80%, 50% to 80%, or 60% to 80%, or preferably, 66% in accordance with the concentration of the plasticizer in the sensitive membrane.

Figure 14A:
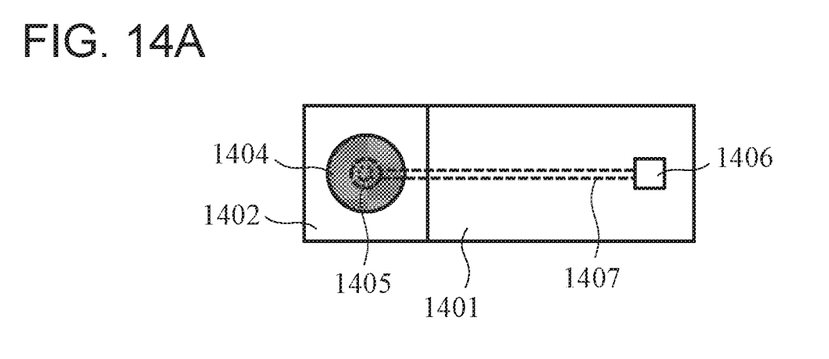
FIGS. 14A and 14B schematically illustrate an example of a solid-electrode-type ISE.
Figure 14B:
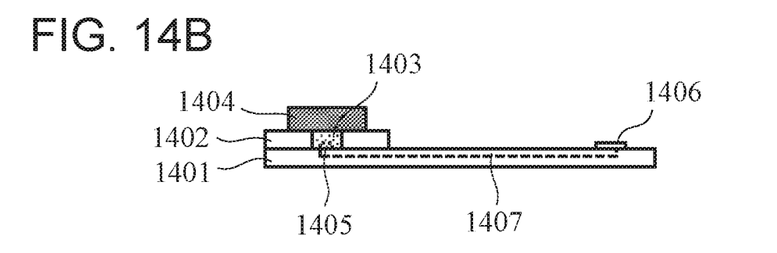

FIG. 14 shows schematic diagrams illustrating another example of the solid-electrode-type ISE in accordance with the present invention. An electrode substrate 1401 includes an electrode 1405 and a terminal 1406, and the electrode 1405 is electrically connected to the terminal 1406 with a wire 1407. The electrode substrate 1401 includes a well 1402, and the well 1402 is filled with a base electrode 1403, and further, an ion-sensitive membrane 1404 is arranged on the base electrode 1403. When the ISE is brought into contact with a solution to be measured together with a reference electrode, and a potential difference between the ISE and the reference electrode is measured, it is possible to determine the concentration of ions that are the measurement targets with the ion-sensitive membrane 1404. For the electrode substrate 1401, it is possible to use a silicon substrate or a resin substrate such as polypropylene (PP), polyethylene (PE), polycarbonate (PC), polyethylene terephthalate (PET), or polyvinyl chloride (PVC). If the electrode substrate 1401 is a silicon substrate, the electrode 1405, the terminal 1406, and the wire 1407 can be found using conductive metal or conductive polysilicon. If the electrode substrate 1401 is resin, the electrode 1405, the terminal 1406, and the wire 1407 can be formed using conductive metal, metal paste, or carbon paste. The well 1402 is preferably formed using resin. If the ion-sensitive membrane 1404 contains PVC, it is possible to increase the degree of adhesion between the well 1402 and the ion-sensitive membrane 1404 by using PVC for the well 1402.

Figure 15A:
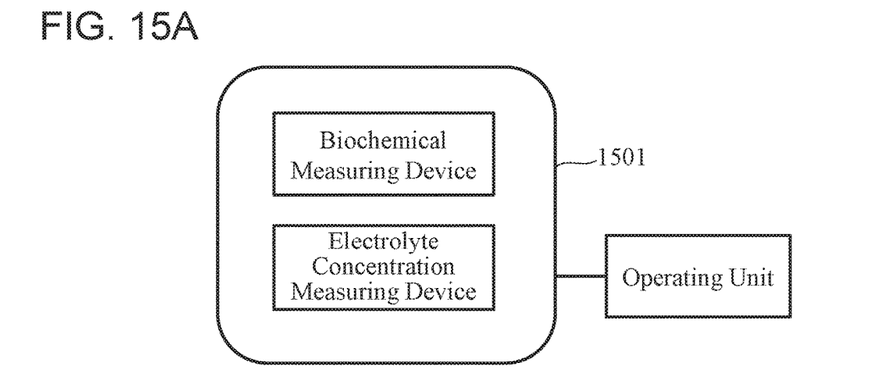
FIGS. 15A and 15B illustrate examples of a system using an electrolyte concentration measuring device.
Figure 15B:
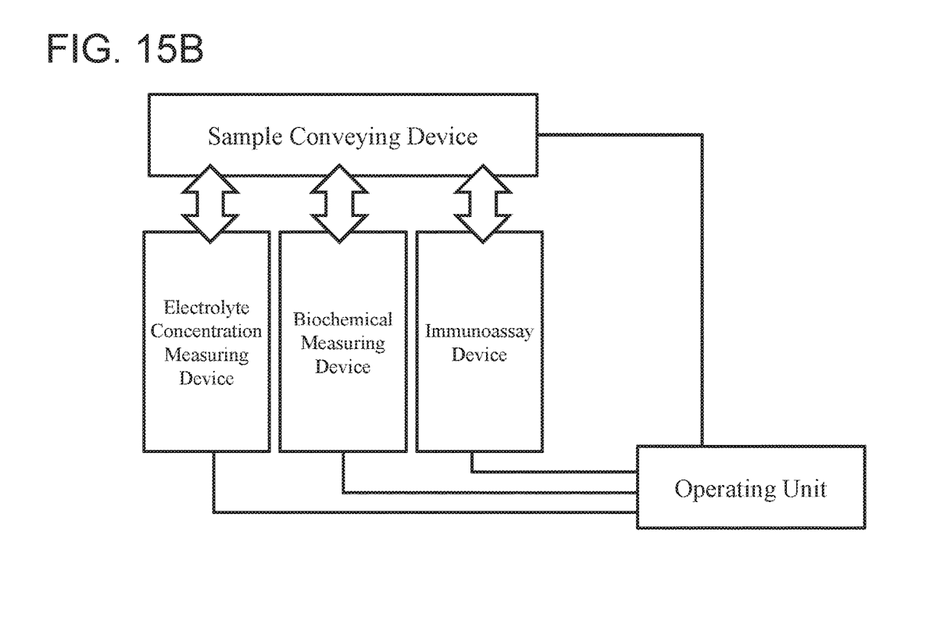

FIG. 15 illustrates examples of a system using an electrolyte concentration measuring device. A biochemical automatic analysis apparatus 1501 shown in FIG. 15(a) mainly includes a biochemical measuring device for optical measurement and an electrolyte concentration measuring device. The biochemical automatic analysis apparatus 1501 can be operated via an operating unit. In FIG. 15(b), devices, such as an electrolyte concentration measuring device, a biochemical measuring device, and an immunoassay device, are independent of each other, and a sample is exchanged between such devices and a sample conveying device. Each device can be operated via an operating unit. If an instruction to measure an ion concentration in a sample is sent from the operating unit, the specified sample is carried into the electrolyte concentration measuring devices in each of FIGS. 15(a) and 15(b), so that the ion concentration is measured and results thereof are output.

The present invention is not limited to the aforementioned embodiments and includes various modifications. For example, although the aforementioned embodiments have been specifically described to clearly illustrate the present invention, the present invention need not include all of the configurations described in the embodiments. It is possible to replace a part of a structure of an embodiment with a structure of another embodiment. In addition, it is also possible to add, to a structure of an embodiment, a structure of another embodiment. Further, it is also possible to, for a part of a structure of each embodiment, add, remove, or substitute a structure of another embodiment.

REFERENCE SIGNS LIST

101 Cartridge of ISE
102 Flow channel
103 Platinum wire
104 Mixture of graphite and liquid oil
105 Sensitive membrane
106 Cover
201 Cartridge of ISE
202 Flow channel
203 Silver-silver chloride electrode
204 Internal solution
205 Sensitive membrane
301 401 Measuring unit
302, 402 Control unit
303, 403 Operation recording unit
304, 404 Output unit
311, 411 Dilution tank
312, 412 Sample dispensing nozzle
313, 413 Diluent dispensing nozzle
314, 414 Internal-standard-solution dispensing nozzle
315, 415 Suction nozzle
316, 321, 416, 420, 423, 426, 428 Pipe
317, 419 Sodium ISE
318, 418 Potassium ISE
319, 417 Chlorine ISE
320, 424 Reference electrode
322, 429 Pump
323, 430 Potential measuring unit
1401 Electrode substrate
1402 Well
1403 Base electrode
1404 Ion-sensitive membrane
1405 Electrode
1406 Terminal
1407 Wire
1501 Biochemical automatic analysis apparatus

The invention claimed is:

1. An electrode for selectively detecting an ion as a measurement target in a measurement solution, the electrode comprising:
    an ion-sensitive membrane adapted to be in contact with the measurement solution;
    a mixture of graphite and liquid oil, the mixture being in contact with the ion-sensitive membrane; and
    a conductor in contact with the mixture of graphite and liquid oil;
    wherein the measurement target is a cation.

2. The electrode according to claim 1, wherein
    the ion-sensitive membrane includes a plasticizer, and
    the liquid oil includes the plasticizer.

3. The electrode according to claim 2, wherein a relative difference between a weight ratio of the plasticizer included in the ion-sensitive membrane and a weight ratio of the plasticizer included in the mixture of graphite and liquid oil is 30% or less.

4. The electrode according to claim 2, wherein
    the ion-sensitive membrane includes a hydrophobic anion, and
    the mixture of graphite and liquid oil includes the hydrophobic anion.

5. The electrode according to claim 2, wherein
    the ion-sensitive membrane includes a substance that selectively binds to the ion as the measurement target, and
    the mixture of graphite and liquid oil includes the substance that selectively binds to the ion as the measurement target.

6. The electrode according to claim 1, wherein the liquid oil is a fluorine-based polymer or fluorine-based oil.

7. The electrode according to claim 1, wherein the graphite is synthetic graphite.

8. An electrode for selectively detecting an ion as a measurement target in a measurement solution, the electrode comprising:
    an electrode substrate containing silicon or resin;
    a conductive electrode formed on the electrode substrate;
    a mixture of graphite and liquid oil, the mixture being in contact with the conductive electrode; and
    an ion-sensitive membrane in contact with the mixture of graphite and liquid oil;
    wherein the measurement target is a cation.

9. A measuring device for measuring a concentration of ions in a measurement solution, the measuring device comprising:
    a plurality of electrodes configured to selectively detect the ions as measurement targets in the measurement solution, wherein each of the plurality of electrodes includes:
        an ion-sensitive membrane adapted to be in contact with the measurement solution;
        a mixture of graphite and liquid oil, the mixture being in contact with the ion-sensitive membrane; and
        a conductor in contact with the mixture of graphite and liquid oil;
    wherein the measurement targets are cations.

* * * * *